United States Patent [19]

Stevens-Wright

[11] Patent Number: 5,383,852
[45] Date of Patent: Jan. 24, 1995

[54] CATHETER WITH INDEPENDENT PROXIMAL AND DISTAL CONTROL

[75] Inventor: Debbie Stevens-Wright, Fitchburg, Mass.

[73] Assignee: C. R. Bard, Inc., Murray Hill, N.J.

[21] Appl. No.: 987,750

[22] Filed: Dec. 4, 1992

[51] Int. Cl.⁶ .............................. A61M 37/00
[52] U.S. Cl. ......................... 604/95; 128/4; 128/642
[58] Field of Search .............. 604/95, 264, 280; 128/4, 6, 642

[56] References Cited

U.S. PATENT DOCUMENTS

| | | | |
|---|---|---|---|
| 2,498,692 | 2/1950 | Mains | 128/348 |
| 3,060,972 | 10/1962 | Sheldon | 138/120 |
| 3,470,876 | 10/1969 | Barchilon | 604/95 |
| 3,605,725 | 9/1971 | Bentov | 128/2.05 R |
| 3,625,200 | 12/1971 | Muller | 128/2.05 R |
| 4,706,681 | 11/1987 | Breyer et al. | 128/642 |
| 4,753,223 | 6/1988 | Bremer | 128/4 |
| 4,758,222 | 7/1988 | McCoy | 604/95 |
| 4,826,087 | 5/1989 | Chinery | 239/551 |
| 4,865,037 | 9/1989 | Chin et al. | 128/419 |
| 4,873,965 | 10/1989 | Danieli | 128/6 |
| 4,906,133 | 10/1990 | Hewson | 128/784 |
| 4,998,916 | 3/1991 | Hammerslag et al. | 604/95 |
| 5,029,585 | 7/1991 | Lieber et al. | 128/642 |
| 5,119,950 | 4/1992 | Schmitt et al. | 604/95 |
| 5,125,896 | 6/1992 | Hojeibane | 604/95 |
| 5,179,935 | 1/1993 | Miyagi | 128/4 |
| 5,195,968 | 3/1993 | Lundquist et al. | 604/95 |

Primary Examiner—C. Fred Rosenbaum
Assistant Examiner—Corrine Maglione
Attorney, Agent, or Firm—Darby & Darby

[57] ABSTRACT

A steerable electrocardial catheter comprises an elongated flexible shaft and a flexible tip assembly connected to the distal end of the shaft. The tip assembly comprises a distal section and a proximal section coaxial with the shaft, the stiffness and length of the distal and proximal sections being selected to provide a predetermined curve configuration of the tip assembly when the distal section and/or proximal section is bent. A first pair of pull cables extending through the catheter is anchored at a first point in the tip assembly for bending the proximal section in a predetermined plane. A second pair of pull cables extending through the catheter is anchored at a second point in the tip assembly for bending the distal section in a predetermined plane. Any desired orientation of the bending planes is possible with the invention. A handle/actuator is also disclosed for applying tension to selected ones of the pull cables for controlling the deflection of the tip assembly.

20 Claims, 7 Drawing Sheets

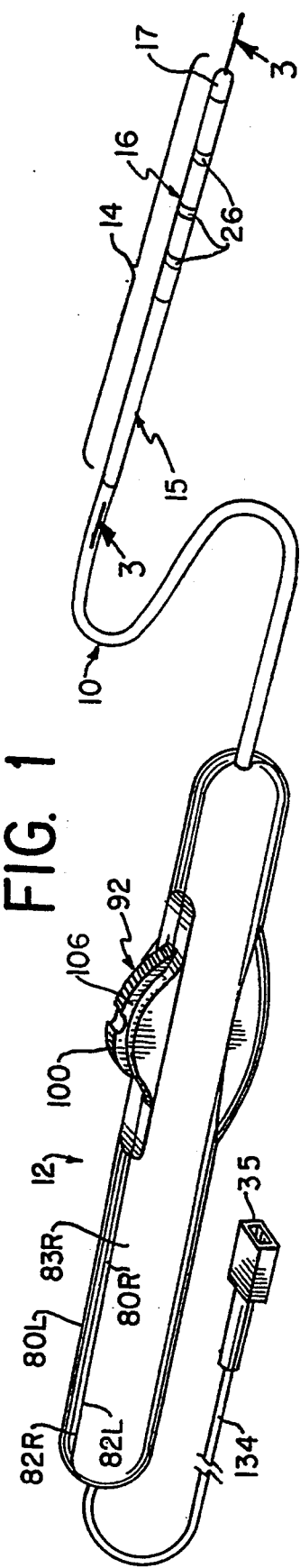
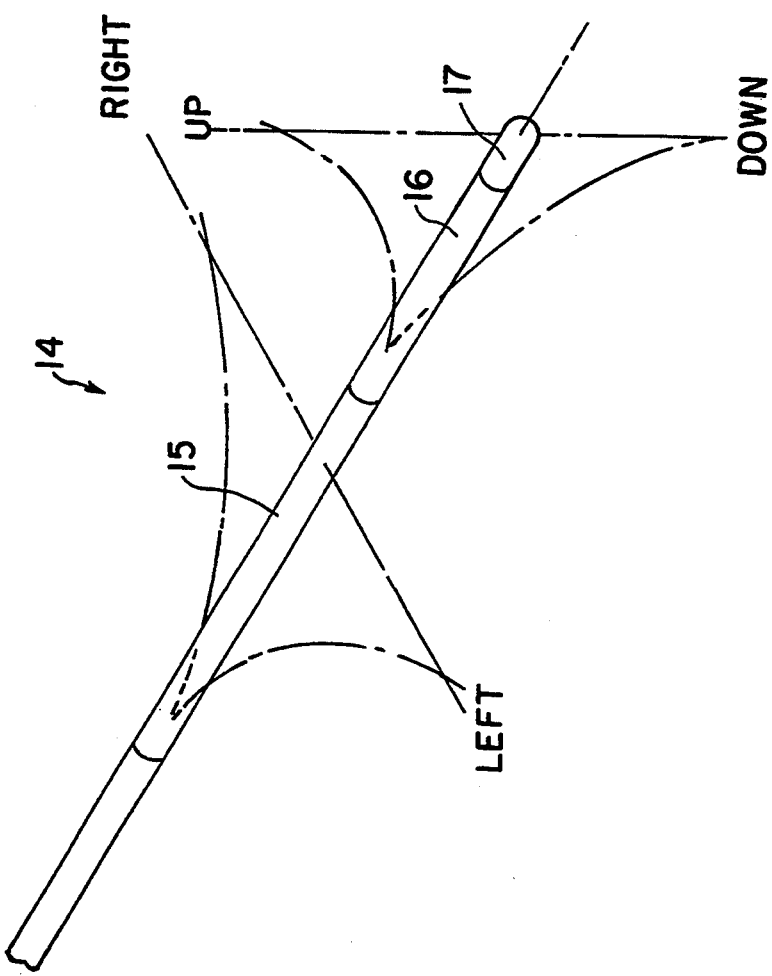

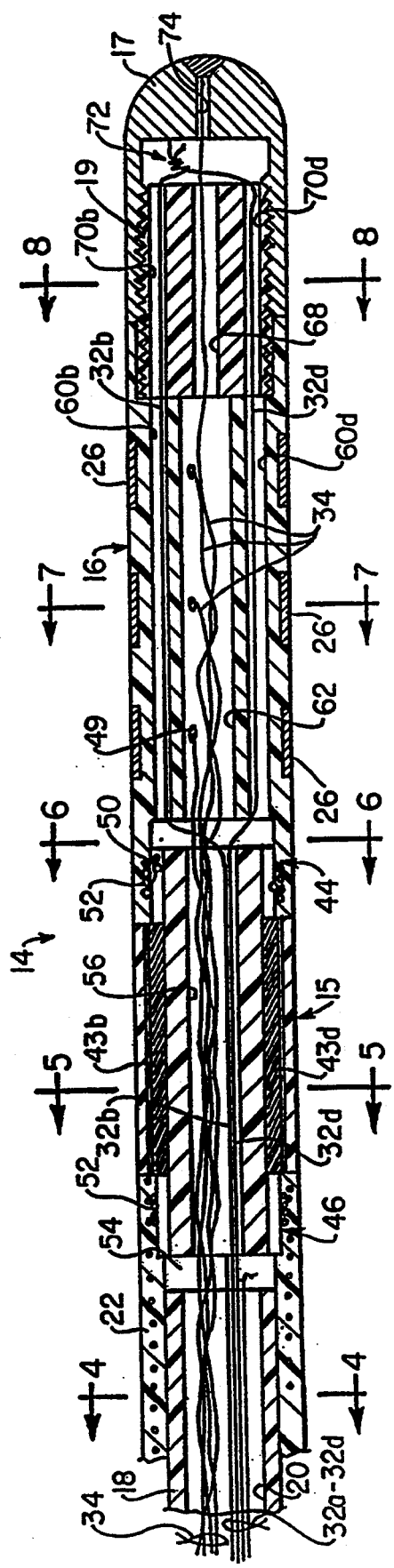
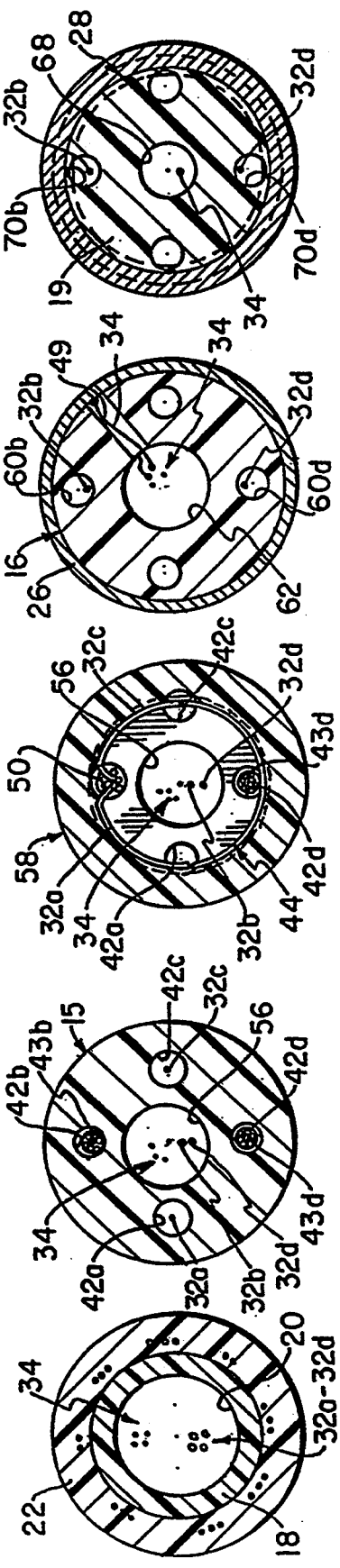

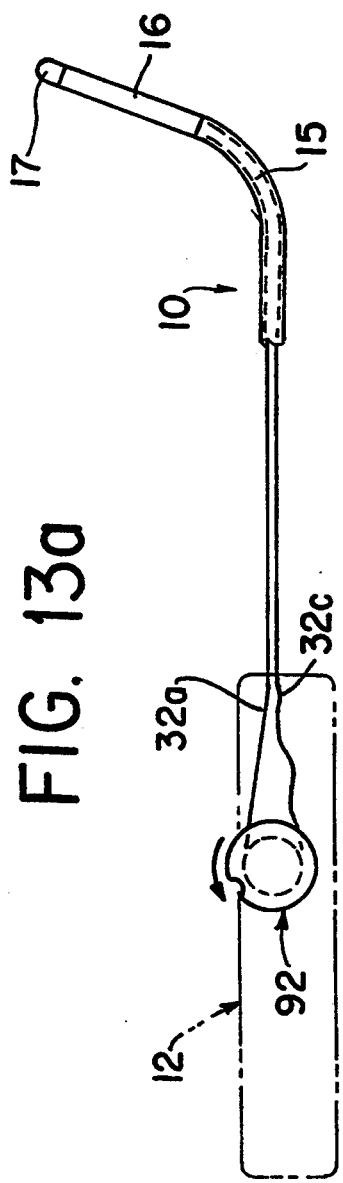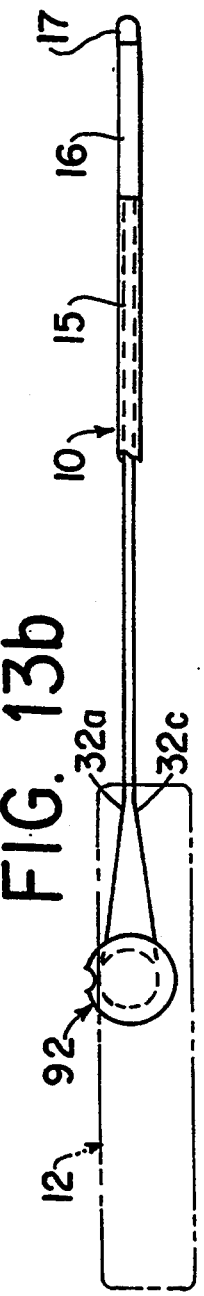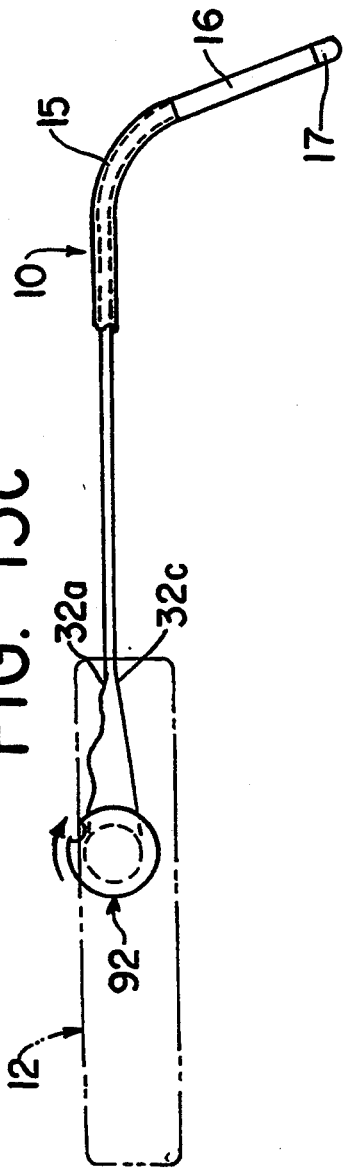

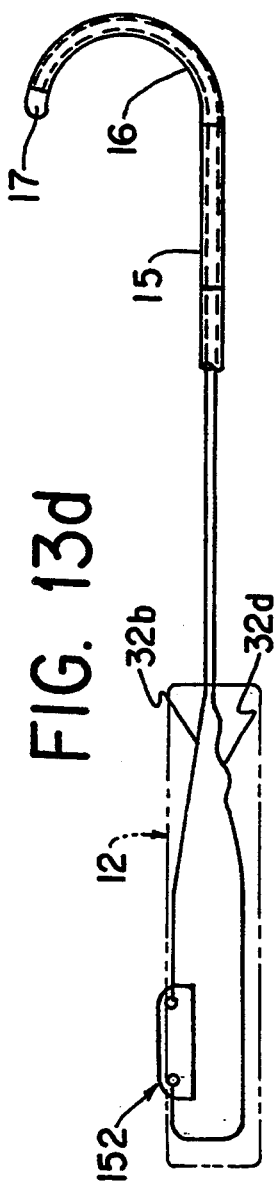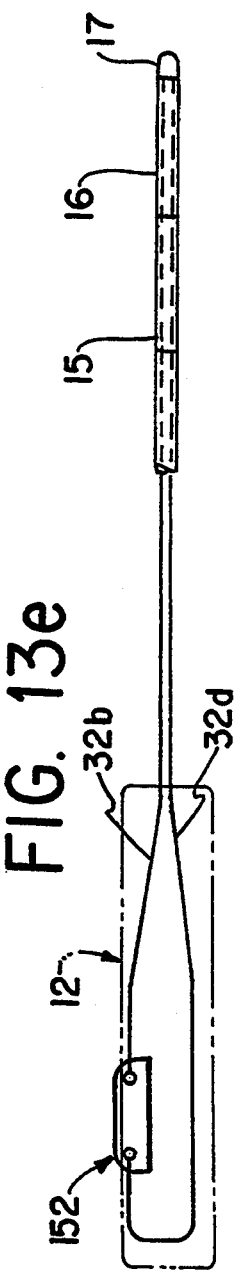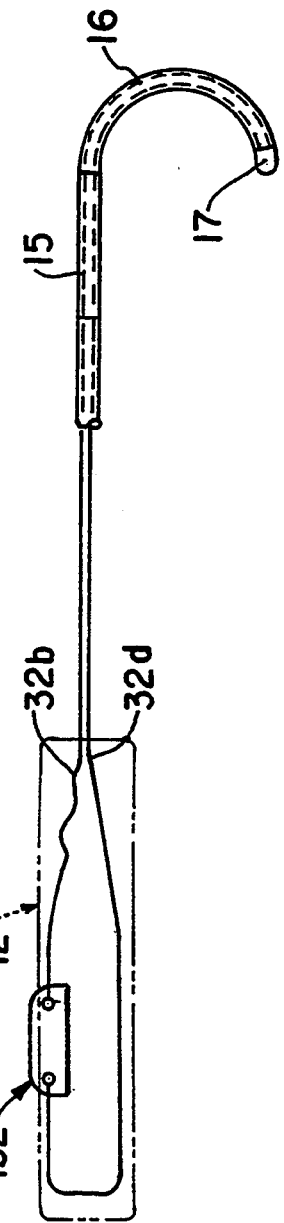

CATHETER WITH INDEPENDENT PROXIMAL AND DISTAL CONTROL

This invention relates to steerable catheters. More particularly, this invention relates to a catheter construction of particular utility for endocardial catheter recording.

FIELD OF THE INVENTION

The clinical role of endocardial catheter recording is to direct ablation, surgical, and drug therapies in the treatment of supraventricular tachycardia, ventricular tachycardia, atrial flutter, atrial fibrillation and other arrhythmias. The success and advancement of current therapies is dependent upon the development and use of more precise localization techniques which will allow accurate anatomical determination of arrhythmogenic sites. Historically, the electrophysiologist has had to compromise between placing the catheter in the place of clinical interest and areas which are anatomically accessible.

Prior art catheter placement has been restricted generally to areas which can be repeatedly accessed by the electrophysiologist. These areas include the HRA (high right atrium), the RVA (right ventricular apex), the coronary sinus and the HIS bundle. To obtain meaningful information about arrhythmogenic sites and reentry circuits with catheters it is imperative that the range of reproducible catheter placement sites be expanded and the number of electrograms recorded over a given area be increased. Some of these additional sites include atrial sites above the tricuspid and mitral valves, ventricular sites circumferential to the mitral and tricuspid valve leaflets, distal areas of the coronary Sinus and great cardiac vein, the AV nodal area and the left ventricle, to name a few.

One area of advancement in improving localization techniques and accessing additional recording sites includes the use of steerable catheters. One type of prior art steerable catheter offers improved maneuverability to specific, otherwise inaccessible sites by providing catheters shaped specifically to access a particular site. Although perhaps useful for some less inaccessible sites, the use of this type of catheter is limited, not very practical, and not helpful in reaching sites requiring active articulation during placement. Three such pre-shaped catheters are described in U.S. Pat. Nos. 3,503,385 issued to Stevens, 3,729,008 issued to Berkovits, and 4,860,769 issued to Forgerty.

Another type of prior art steerable catheter attempts to improve placement maneuverability by providing catheters having deflecting tips. These catheters include a soft and flexible distal portion of a certain length attached to a proximal shaft made from a stiffer material. The tip may be selectively deflected but only in a prescribed arc, i.e., the tip bends in one planar direction. Examples of deflecting tip catheters are described in U.S. Pat. Nos. 4,920,980 issued to Jackowski, 4,960,411 issued to Buchbinder, and 4,960,134 issued to Webster.

The main disadvantage of the above-described preformed and deflecting tip type catheters is that the tip of the catheter in each case may be steered only in a prescribed manner which cannot be altered during its placement. This restriction of steering of these types of prior art catheters limits their effectiveness in reaching many of the desired recording sites.

Many of the desired sites require that the catheter traverse paths having many sharp bends and be able to negotiate multiple changes of direction through any or all of the three perpendicular planes of movement. Four-way steerable catheters have been developed in an attempt to provide a catheter with the above-described multi-planar maneuverability. As examples, such four-way steerable catheters are described in U.S. Pat. Nos. 3,470,876 issued to Barchilon, and 4,921,482, 4,998,916 and 5,037,391 issued to Hammerslag.

Typically, a four-way steerable catheter operates in two perpendicular planes of direction, with two control cables operating the tip in each plane of movement. One of the problems associated with these prior art bi-planar steering catheters resides in the steering actuator. The four cables extend back through lumens in the catheter to the handle. The prior art devices show that each cable pair may be manipulated using a variety of mechanical actuators such as slide levers, gear trains, or a single thumb wheel pulley, each being operated manually or using a motor. For the most part, these actuators function, but they are expensive to manufacture and difficult or cumbersome to use.

OBJECTS OF THE INVENTION

The main object of the invention is to provide an improved endocardial catheter.

Another object of the invention is to provide a steerable catheter which overcomes and/or alleviates the problems of the prior art.

Still another object of the invention is to provide a steerable catheter which can negotiate paths traversing a multi-planar space with relative ease.

Yet another object of the invention is to provide a steerable catheter which can be easily and accurately operated by suitable handle controls.

SUMMARY OF THE INVENTION

According to the invention, a steerable catheter comprises an elongated flexible shaft and a flexible tip assembly connected to the distal end of the shaft. The tip assembly comprises a distal section and a proximal section coaxial with the shaft. The proximal and distal sections can be separately bent to provide distal and proximal bending of the catheter. The stiffness and length of the distal and proximal sections may be selected to provide independent proximal and distal bending and a predetermined curve configuration of the tip assembly when the distal section and/or proximal section is bent.

BRIEF DESCRIPTION OF THE DRAWINGS

FIG. 1 is a perspective view of a multi-jointed steerable catheter according to a preferred embodiment of the invention;

FIG. 2 is a diagrammatic perspective view of a tip assembly of the catheter showing proximal and distal bending in horizontal and vertical planes;

FIG. 3 is a longitudinal section along the line 3—3 of FIG. 1;

FIGS. 4–8 are transverse sections along lines 4—4 through 8—8 of FIG. 3;

FIGS. 13a, b and c are diagrammatic illustrations showing proximal bending movement of the tip assembly;

FIGS. 13d, e and f are diagrammatic illustrations showing distal bending movement of the tip assembly;

DETAILED DESCRIPTION OF THE PREFERRED EMBODIMENTS

Figure 9:
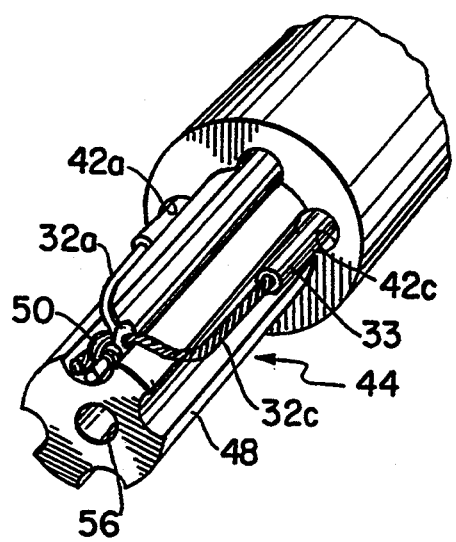
FIGS. 9–10 are perspective views showing one way of anchoring a cable within the tip assembly.

A steerable electrode catheter in accordance with a preferred embodiment of the invention comprises an elongated flexible shaft 10, a handle/actuator 12 and a tip assembly 14 (FIG. 1). As described below, the user manipulates the tip assembly 14 by means of the handle/actuator 12 and control cables which pass through the shaft 10.

In the preferred embodiment, the tip assembly 14 comprises a tubular proximal section 15 and a tubular distal section 16 aligned coaxially with the shaft 10 and of approximately the same outer diameter. The distal end of the catheter terminates in an electrode cap 17 which is also coaxially aligned with the shaft 10 and sections 15 and 16. A threaded collar 19 is secured to the distal end of distal section 16 to retain the electrode cap 17 as described further below.

Shaft 10 includes a core 18 (FIG. 3) having a single lumen 20 which extends the length of the shaft from the distal end of the handle actuator 12. As described in greater detail below, the single-lumen 20, in this preferred embodiment, holds four pull cables 32a, b, c and d and four electrode signal wires 34. The core 18 is enclosed in a flexible outer protective sheath 22. The core 18 with its outer protective sheath 22 has a predetermined degree of rigidity which depends on the intended use of the catheter.

The steerable electrode catheter assembly may be viewed as including mechanical and electrical sub-assemblies. The mechanical sub-assembly is a remote steering system which includes the handle actuator 12 connected to the four pull cables 32a, 32b, 32c and 32d which run the length of shaft 10 within lumen 20 of core 18. The distal ends of the pull cables 32 are connected to various points of the tip assembly 14 as described below. The pull cables 32 translate handle actuator manipulation by the working electrophysiologist through the length of the shaft 10 into single or multi-planar, proximal and/or distal bending movement of the tip assembly 14 as described below. Each pull cable 32 preferably includes a sheath 33 (shown only in FIGS. 9–12).

The electrical portion of the steerable electrode catheter assembly includes three spaced ring-type electrodes 26 along with electrode cap 17. The electrodes provide signal information on heart potentials to remote recording equipment (not shown) used by the electrophysiologist. The ring-type electrode contacts 26 and the electrode cap 17 are electrically connected to respective signal wires 34. The signal wires 34 are routed through the length of core 18 through lumen 20, as illustrated in FIGS. 3 and 4. The signal wires 34 are preferably electrically insulated from each other and therefore may all share a single lumen as shown in FIGS. 4–8. The signal wires 34 extend proximally through the handle/actuator 12 to a connector 35 which enables the electrodes 26 and 17 to be easily coupled electrically to the recording equipment (not shown).

In the illustrated embodiment of the invention, two pull cables 32a and 32c (referred to in this description as a horizontal pull-cable pair) are used to control bending of the proximal section 15 within a horizontal plane of orientation as shown diagrammatically in FIG. 2. The other two pull cables 32b and 32d (referred to in this description as a vertical pull-cable pair) are used to control bending of the distal section 16 within a vertical plane of orientation. Thus, in the illustrated embodiment, left-right proximal bending and/or up-down distal bending of the tip assembly are possible.

Although the illustrated embodiment provides perpendicular planes of proximal and distal movement, the relative orientation between these two planes may vary with different catheter applications and desired tip-shapes and the two planes may form angles between zero degrees and one hundred eighty degrees. By varying the angle of intersection between the two planes, one catheter tip arrangement, for example a two-dimensional arrangement (where both planes are coplanar), may be bent into a specific shape (such as a spiral) within the single plane of movement. If the first and second planes of orientation of the respective proximal and distal bending movements intersect at ninety degrees (as illustrated in FIG. 2), the resulting catheter tip may be manipulated into several two and three-dimensional shapes including a three-dimensional spiral cone.

The proximal section 15 includes a central lumen 56 (FIG. 5) for passing pull cables 32b and 32d and all of the signal wires 34 from the lumen 20 of core 18 to the distal section 16. The proximal section 15 also includes two proximal cable lumens 42a and 42c which pass pull cables 32a and 32c from the lumen 20 of the core 18 through the length of the proximal section 15. Proximal cable lumens 42b and 42d may contain respective stiffening wires 43b and 43d to reduce axial twisting of proximal section 15. The proximal section 15 includes reduced diameter ends 44 and 46 so that the proximal section 15 may snugly nest into appropriately cored recesses of the protective sheath 22 and the distal section 16, respectively.

Proximal bending is controlled by the pull cables 32a and 32c. These two cables extend from lumen 20 of core 18 through lumens 42a and 42c in proximal section 15 as shown in FIG. 5. Cables 32a and 32c are attached to each other at the distal end 44 of proximal section 14 as described below.

The proximal section 15 is thermally bonded to the distal end of the protective sheath 22. The core 18 is shorter in length than the protective sheath so that a transition space 54 is created between the distal end of core 18 and the proximal end of the proximal section 15. The transition space 54 allows the signal wires 34 and the pull cables 32 to be radially displaced, as discussed below.

Figure 10:
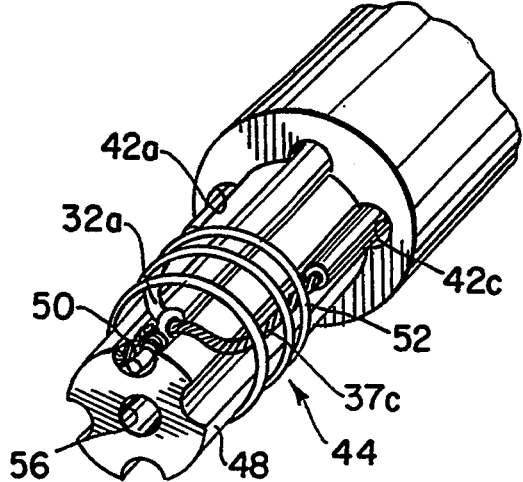

Referring to FIGS. 6, 9 and 10, the pull cables 32a and 32c are tied to each other to form a knot 50 across the reduced diameter end 44 of proximal section 15. Knot 50 preferably lies within the channel-like remains of a proximal cable lumen 42 intersecting the reduced diameter end 44. As shown in FIG. 10, strain relief wire 52 is wrapped around both the reduced diameter end 44 and the knot 50 to anchor the ends of the pull cables 32a and 32c to the proximal section 15. The knot 50 and the strain relief wire 52 are potted in place using an appropriate potting material (not shown) such as an epoxy. When the pull cables 32a and 32c are pulled, the strain relief wire 52 helps to distribute a portion of the resulting strain, thereby preventing the knot 50 from failing.

Figure 11:
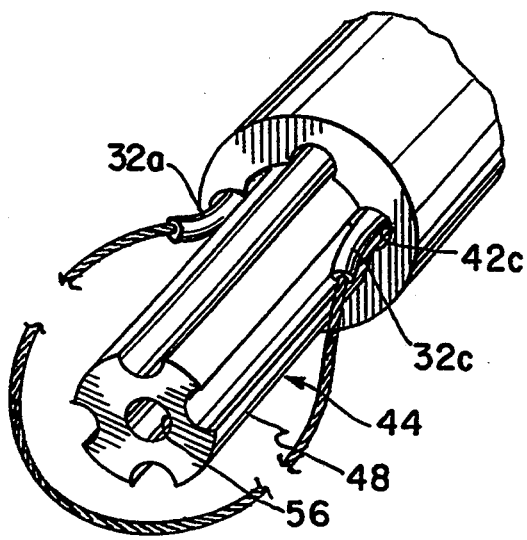
FIGS. 11 and 12 are perspective views showing a second way of anchoring a cable within the tip assembly.
Figure 12:
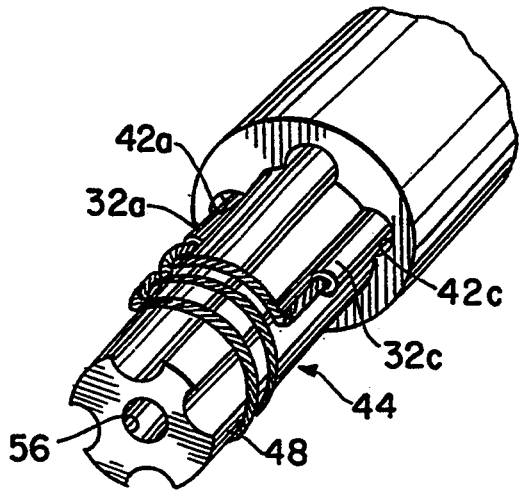

In another related embodiment, illustrated in FIGS. 11 and 12, the pull cables 32a and 32c are introduced as a single pull cable. In this embodiment, the two ends of the pull cable are fed into the corresponding proximal cable lumen 42a, 42c and then through the main pull cable lumen 20 of shaft 10 to the handle actuator. The resulting loop of pull cable (shown in FIG. 11) formed at the distal end 44 of the proximal section 15 is stripped of its sheath, wrapped (coiled) around the reduced diameter end 44 (FIG. 12), and potted into position. This embodiment eliminates the need to knot the pull cable ends because the pull cable ends are already attached to each other.

To develop greater bending leverage, the cable lumens 42a and 42c through which cables 32a and 32c pass are located as close as possible to the circumference of the proximal section 15.

The distal section 16 includes two cable lumens 60b and 60d and a central lumen 62 (FIG. 7). Pull cables 32b and 32d from the central proximal section lumen 56 are routed to the outwardly disposed cable lumens 60b and 60d, respectively, at a point just past the distal end of the proximal section 15.

In the preferred embodiment, the three ring-type electrode contacts 26 are embedded within the outside wall portion of the distal section 16. It is preferred that these electrode contacts be embedded so that the outer surface of each contact 26 is flush with the outer wall. These electrode contacts 26 (and others if used) may be positioned anywhere along the entire length of the shaft 10 or the tip assembly 14. The signal wires 34 which have been routed from the central proximal section lumen 56 into the central lumen 62 of the distal section 16 are directed through respective holes 49 (FIG. 7) to their respective ring-type electrode contacts 26, and connected thereto in a conventional manner, i.e., by soldering or welding.

Collar 19 includes a central lumen 68 and at least two outer cable lumens 70b and 70d (FIG. 8). The central lumen 68 receives the last remaining electrode signal wire 34, while the cable lumens 70b and 70d direct the pull cables 32b and 32d distally to their anchoring point. Pull cables 32b and 32d are tied to each other at a point just past the distal end of the threaded collar 19 to form a knot 72. The knot 72 is further secured by applying an adhesive, such as an ultra-violet activated adhesive.

The electrode cap 17 includes a hollow threaded recess which engages the external threads of collar 19. Electrode cap 17 includes a central opening 74 which receives the last remaining signal wire 34 of this preferred embodiment. The signal wire 34 may be electrically connected to the electrode cap 17 by any conventional method, such as soldering or welding.

A steerable catheter, in accordance with the invention, provides for both proximal and distal bending by pulling selected ones of the pull cables 32a, b, c or d. In the preferred embodiment, proximal and distal bending of the catheter are essentially independent, i.e., bending of the distal section 16 does not cause bending of proximal section 15 (or shaft 10) and vice versa. The bending of either section 15 or 16 is generally analogous to the bending of a cantilevered beam in the sense that one end of either section (i.e., the proximal end) is fixed while the entire section bends as tension is applied to a cable attached to the opposite end. To provide this result, it is necessary that the shaft 10 be stiffer than proximal section 15 and that the proximal section 15 be stiffer than the distal section 16. The extent to which the stiffness of these various sections must differ to provide independent proximal and distal bending can be determined empirically and the example below provides representative values which have been found to work in practice for the configuration illustrated. If independent proximal and distal bending is not desired, the difference in stiffness between the sections is not critical; it is at least theoretically possible that the distal section could be stiffer than the proximal section.

In the preferred embodiment, with the materials and hardnesses indicated below, tension applied to cable 32a or 32c causes the proximal section 15 to bend horizontally (i.e., in and out of the plane of the paper) about reduced diameter end 46. Because of the hardness differential between the proximal section 15 and shaft 10, the shaft 10 does not bend significantly. There is no tendency of the distal section 16 to bend in this case.

When tension is applied to one of the cables 32b or 32d, the distal section 16 is bent in a vertical plane (i.e., in the plane of the paper) about the reduced diameter end 44 of proximal section 15. This vertical bending of the distal section occurs regardless of the condition of the proximal section 15. Again, if the differential in hardness between sections 15 and 16 is sufficient, bending of distal section 16 will not cause substantial bending of either proximal section 15 or shaft 10.

The radius of curvature of each of the sections 15 and 16 is, of course, affected by the length of the section. Representative values of section lengths are also given below.

Various configurations can be used to locate and anchor the pull cables within the shaft and the proximal and distal sections of the catheter tip assembly. It is preferable to conduct the pull cables as close as possible to the outer circumference of the section controlled by the cables in order to increase the bending moment. For this reason, the controlling push pull cables for both the proximal and distal sections are directed to outer lumens, i.e., lumens 42a, 42c and lumens 60b, 60d. The illustrated construction has been found to be an optimal arrangement from the points of view of manufacturing ease and function. Other arrangements, however, can also be used. For example, the pull cables can be conducted through the proximal and distal sections exclusively through outer lumens. The wires 34 may be conducted through separate lumens, including a single designated outer lumen. The cables and wires also can be conducted along channels which can be closed by an appropriate covering. It is contemplated that the various tubular sections, including the core and the proximal and distal sections will be extruded.

The following portion of this specification states preferred materials, dimensions and hardness characteristics for the structure illustrated in FIGS. 1 and 3-8.

Shaft 10 may be an extruded polyether block amide of the type sold by Atochem North America, Inc. under the trademark PEBAX (hardness 72-63 Shore D). A typical length is about 110-120 cm with an outer diameter of 0.092 inch (7 French). The sheath 22 may comprise the same material with an embedded stainless steel braid to enhance stiffness.

The proximal section 15 may also be an extrusion of PEBAX elastomer (hardness 55 Shore D). Alternatively, it may be made of PELLETHANE urethane elastomer supplied by Dow Chemical Company.

The length of the proximal section 15 may be 1.5–8.0 cm with the reduced diameter ends 44 and 46 each extending an additional 4 mm. The outer diameter of section 15 may be 0.092 inch with the ends 44 and 46 ground down to a diameter of about 0.067 inches. The stiffening wires 43b and 43d may be 0.009 inch copper wire.

The distal section 16, also an extrusion, may be made of PELLETHANE elastomer (hardness 90 Shore A). Its length may be 2.0–8.0 cm.

The cables 32a, b, c and d may each comprise a multiplicity of ultra-high molecular weight polyethylene filaments, each forming a bundle with a diameter in the range of 0.003–0.004 inches. Sheath 33 may be made of polytetrafluoroethylene (TEFLON brand) with an outer diameter of 0.014 inch and an inner diameter of 0.010 inch.

Collar 19 may be a polycarbonate or ABS plastic. It may be bonded to the distal section 16 by an adhesive or by thermal bonding.

The electrodes 17 and 26 may be made of any appropriate electrode contact metal, such as platinum.

Catheter Assembly

To assemble the catheter, the wires 34 are welded to the electrodes 26. The distal end of the distal section 16 is tapered and the proximal end of the distal section 16 is cored to a diameter of 0.67 inch. The holes 49 for wires 34 are formed in the distal section 16 and the section pulled to reduce its diameter so the electrodes rings can be slid into position and the wires 34 threaded through the holes. The tapered end is then cut to length and cored to a diameter of 0.67 inch.

Both ends of the proximal section 15 are ground to a diameter of 0.67 inch. The shaft 10 is then cored to a diameter of 0.67 inch and out to length. Proximal section 15 is then inserted into the cored end of shaft 10 and thermally welded.

The cables 32 are conditioned to rid them of "creep" and stretch. This is done by cyclically loading the cables by the application of a specified tensile force. The cables 32 are then threaded through their respective lumens in the shaft 10 and sections 15 and 16.

Cables 32a and 32c are anchored as described above to reduced diameter end 44 of proximal section 15. The distal section 16 is then secured to the proximal section 15, also by thermal welding.

The cables 32 are threaded through and secured to collar 19. One of the wires 34 is welded to the electrode cap 17. The wire is then threaded into the catheter and the electrode cap 17 screwed onto the collar 19. The electrode cap 17 and the collar 19 are then inserted into the distal section 16.

A ring of adhesive is applied around the edges of the electrodes to provide smooth transitions at the electrodes and to seal the electrodes. The assembled catheter with the electrical wires 34 and pull cables 32a, b, c and d extending from its proximal end may then be attached to the handle/actuator 12 which is described in the following section of the specification.

The Handle/Actuator

The handle/actuator 12 applies tension selectively to one of the four pull cables 32a, b, c and d and also routes the electrical wires 34 to the appropriate instruments. The handle requires separate controls for the proximal and distal bending, respectively, and these controls should be easily distinguishable by the surgeon during use. As is customary, the entire handle may be rotated during use to apply a torquing force to the catheter; therefore, the individual controls should be easily accessible when the handle is rotated. All required manipulations should be consistent regardless of the position of the handle or its placement.

Preferably, both steering controls should be actuable without requiring substantial hand movements and the handle should provide for near simultaneous actuation of both proximal and distal steering.

The handle must be able to meet all appropriate environmental and sterility requirements likely to be encountered. Preferably, it provides a mechanical advantage. The handle should be able to hold the tip assembly in a bent or deflected condition until the surgeon actively changes deflection. The mechanism should be able to compensate for stretching of the pull cables likely to be encountered during normal use.

Figure 14:
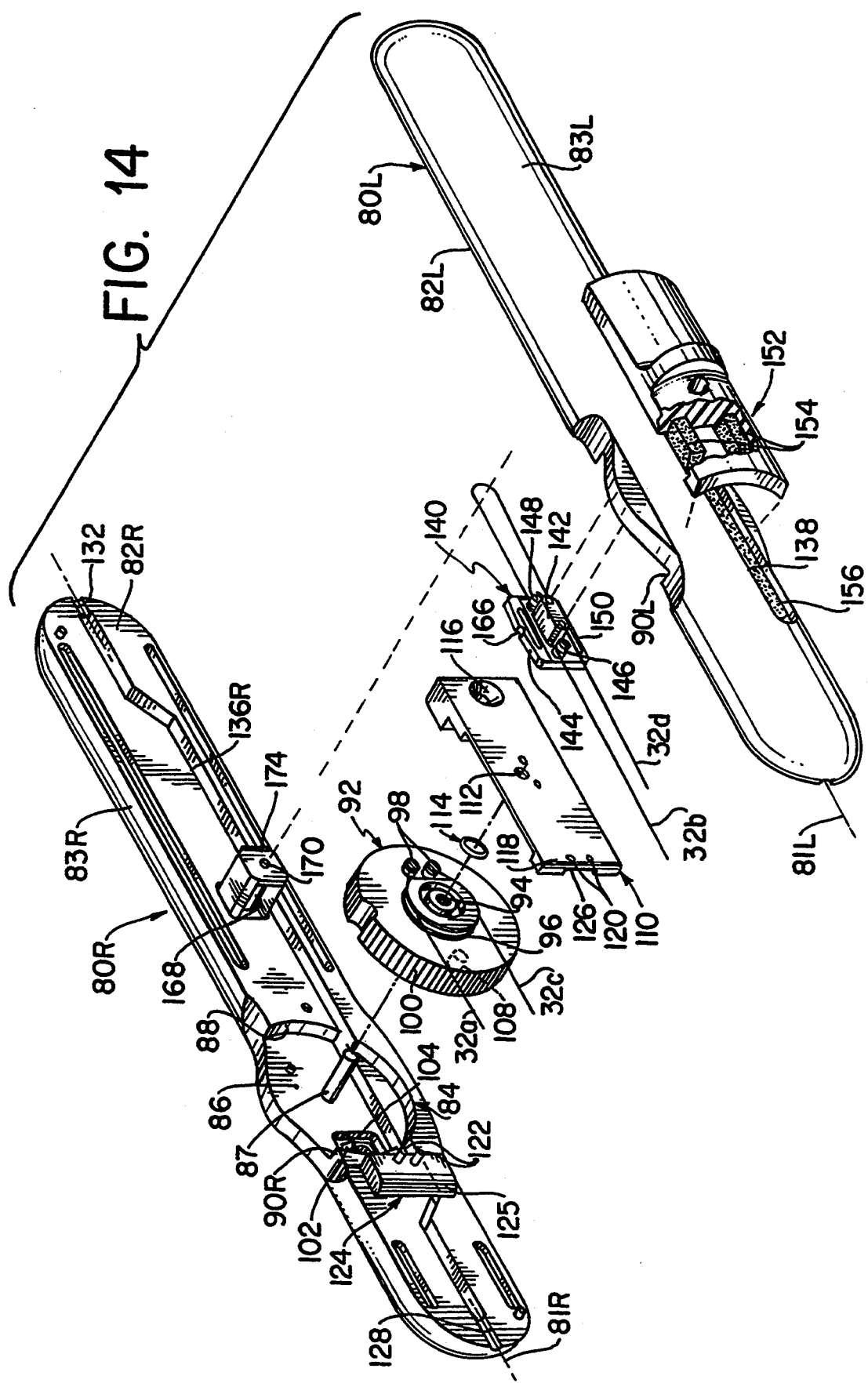
FIG. 14 is an exploded perspective view of a preferred cable control mechanism for use with the invention.
Figure 15:
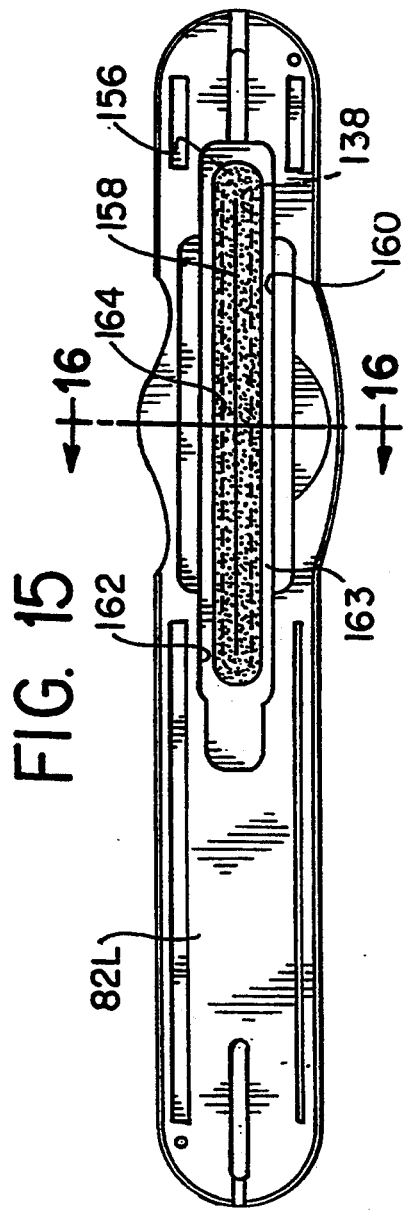
FIG. 15 is a plan view of a section of the handle/actuator shown in FIG. 14.
Figure 16:
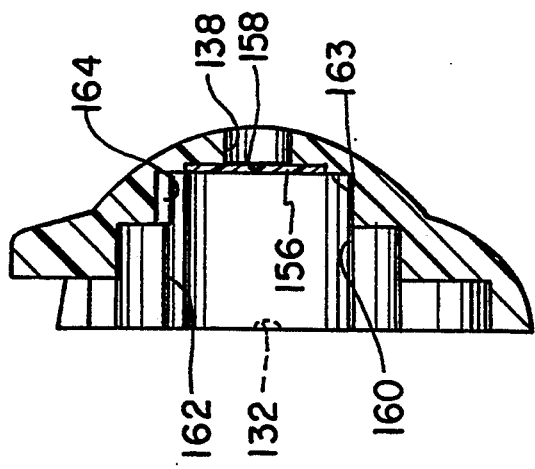
FIG. 16 is a sectional view along the line 16—16 of FIG. 15.

A handle/actuator assembly which is capable of achieving the foregoing objectives is shown in FIGS. 14–16. The handle configuration shown in these drawings uses rotational movement to control selectively the tension applied to the horizontal pull cables 32a and 32c, and linear movement to control selectively the tension applied to the vertical pull cables 32b and 32d.

Referring to FIGS. 14–16, the handle/actuator 12 comprises two half sections: a left section 80L and a right section 80R, shown having longitudinal axes 81R, 81L, respectively. In accordance with the preferred embodiment of the invention, these two sections 80L and 80R are somewhat semicircular in cross section (FIG. 16) and have flat connecting surfaces 82L and 82R which may be secured to each other along a common plane to form the complete handle/actuator 12. The outer surfaces 83L and 83R of the handle/actuator 12 are contoured to be comfortably held by the user.

A wheel cavity 84 is formed within the right section 80R of the handle/actuator 12. The wheel cavity 84 includes a planar rear surface 86 which is generally parallel to the flat surface 82R and an arcuate wall section 88 which extends perpendicularly between the planar rear surface 86 and the flat surface 82R. The wall section 88 terminates at the intersection of the adjacent outer surface 83 of the right handle section 80R and provides a wheel access opening 90R. The wheel cavity 84 also includes a central shaft 87 which protrudes perpendicularly from the planar rear surface 86 and extends toward the left section 80L to function as a support for a thumbwheel 92.

The thumbwheel 92 is a generally circular disc having a central bore 94, an integrally formed pulley 96, and upper and lower cable anchors 98. The thumbwheel 92 is positioned about the shaft 87 so that it may rotate freely within the wheel cavity 84. The pulley 96 of the thumbwheel 92 is centrally formed about the central bore 94 and operates within a pulley plane which is parallel to the planar rear surface 86. A peripheral edge surface 100 of the thumbwheel 92 protrudes from the wheel access opening 90 so that the thumbwheel 92 may be rotated by the thumb of the operator's hand which is used to grip the handle 12. To ensure a positive grip between the thumbwheel 92 and the user's thumb, the peripheral edge surface 100 of the thumbwheel 92 is preferably serrated, or otherwise roughened.

The thumbwheel 92 includes an indicator of a neutral position wherein, for example, the two pull cables 32a, 32c which are connected to the thumbwheel 92 are both equally tensioned and the corresponding section of the tip assembly 14 is in its relaxed position. A neutral position indicator is provided using a positive detent engagement between the thumbwheel 92 and a portion of the housing 12. A detent spring 102 is provided within a spring recess 104 formed in the planar rear surface 86 of the wheel cavity 84. A contact portion of the detent spring 102 projects into frictional contact with the adjacent side surface of the thumbwheel 92. A detent 108 is formed within the side surface 106 of the thumbwheel 92 so that in the neutral position of thumbwheel 92 the detent 108 receives the contact portion of the detent spring 102 resulting in a point of high-friction which provides an indication of the neutral position of the thumbwheel 92.

A cover plate 110 is attached to the flat connecting surface 82R of the right handle section 12R retaining the thumbwheel 92 in its mounted position on the central shaft 87 and within the wheel cavity 84. The cover plate 110 is preferably made from a rigid material such as metal or hard plastic. The cover plate 110 includes an opening 112 to receive the central shaft 87. An O-ring 114 is positioned between the cover plate 110 and the thumbwheel 92. The cover plate 110 is attached to the right handle section 80R at a proximal secured end 116 by a bolt or screw so that a controlled amount of friction resistance is imparted to the thumbwheel 92 by compressing the O-ring 114. Such a rotational resistance is used to maintain the thumbwheel 92 in a particular angular position and therefore also maintain a particular bend at the tip assembly 14.

The distal end 118 of the cover plate 110 includes two openings 120 to receive two corresponding alignment dowels 122 extending from section 80R. The alignment dowels 122 are secured to a cable guide 124 which, in turn, is attached to the flat surface 82R. The dowels 122 are preferably press-fit into the two openings 120.

The cable guide 124 is used to divert the pull cables 32a and 32c from the core 10 to the plane of pulley 96 as described below. The cable guide 124 has a smooth curved forward surface 125 which prevents contact trauma to the delicate pull cables as they are diverted.

A gap 126 is provided between the cable guide 124 and the free end 118 of the cover plate 110. The gap 126 is sized to receive the two pull cables 32a and 32c and lies within the abovementioned plane of pulley 96. The pulley plane is a prescribed distance from the flat connecting surface 82R of the right handle section 80R.

A distal opening 128 is provided within the distal end of the handle/actuator 12 and is centered along the longitudinal axis 81 (the formation of the forward opening 128 is shared between the right and left sections 80R and 80L). The forward opening 128 is adapted to snugly receive shaft 10 which is secured within the opening. 128 by an appropriate adhesive. A proximal opening 132 centered on the longitudinal axis 81 is also split between the right and left handle sections 80R and 80L). The proximal opening 132 is adapted to snugly receive an electrical conduit 134 (see FIG. 1) containing electrical signal/recorder wires 135 to be connected to appropriate recording equipment (not shown).

Channels 136R and 136L are formed (preferably integrally) within the right and the left sections 80R, 80L, respectively, of the handle/actuator 12. When the right and left handle sections are assembled, the resulting complete channel 136 connects the distal opening 128 to the proximal opening 132. The channels 136R, 136L are not necessarily formed along the longitudinal axis 81, but may be routed to avoid other elements mounted between the two handle sections 80R and 80L.

The proximal end of the tubular shaft 10 terminates near the distal end of the handle/actuator 12 so that the four electrode signal wires 34 and the four pull wires 32 may be distributed as necessary. The four electrode signal wires 34 are routed through the channel 136 and are electrically connected to the appropriate signal/recorder wires 135 of the electrical conduit 134.

The pull cables are separated into horizontal and vertical pull cable pairs 32a, 32c and 32b, 32d, respectively. Pull cables 32a and 32c are positioned within the gap 126 between the cable guide 124 and cable plate 110, and also between the two alignment dowels 122. The two pull cables 32a and 32c which control proximal bending of proximal section 15 are connected to the cable anchors 98. The cable anchors 98 are conventional bolt-type arrangements. The cables are wrapped around the anchors and potted into place using an UV adhesive. One pull cable 32a, which is connected to the upper cable anchor 98, is positioned within the groove of the pulley 96 so that it rides over the pulley 96 and contacts the upper of the two alignment dowels 122 when pulled taut. The other pull cable 32c is connected to the lower cable anchor 98 and is positioned within the pulley groove so that it rides below the pulley 96 and contacts the lower alignment dowel 122 when taut.

The left section 80L of the handle/actuator 12 includes a substantially hollow interior cavity which is shaped to cover the above-described elements. The left section 80L also supports some of the parts of the mechanism for selectively tensioning each of the two vertical pull cables 32b and 32d.

To accommodate the protruding portion of the thumbwheel 92, the left handle section 80L includes a wheel access opening 90L similar in shape to the wheel access opening 90R of the right handle section 80R. It also includes an elongated slot 138 in its side surface.

A slider 140 is provided with a neck portion 142 which fits snugly within the slot 138. The slider 140 includes an upper edge 144, a forward cable anchor 146, a rear cable anchor 148, and a friction pad 150. A slider grip 152 is attached to the neck portion 142 of the slider 140 and positioned externally of the handle/actuator 12. The slider grip 152 is preferably ergonometrically shaped to be comfortably controlled by the user. Preload pads 154 are positioned between the outer surface 83L of the left handle section 80L and the slider grip 152. The friction pad 150 functions to provide constant friction during sliding movement of the slider 140 and the slider grip 152 so that any desired position is maintained until the friction of the friction pad 150 is overcome, e.g., by physically repositioning the slider grip 152.

A lip seal 156 (FIGS. 15 and 16) having an elongated slit 158 and preferably made from latex is bonded along the slot 138 within the left handle section 80L. The neck portion 142 of the slider 140 protrudes through the slit 158 of the lip seal 156 so that the slit only separates adjacent to the neck portion 142. Otherwise, the slit 158 remains "closed" and functions as an effective barrier preventing dust, hair and other contaminants from entering the actuator/handle 12.

The left handle section 80L includes a slider chamber 160 (FIG. 15) which aligns with and is centered about the slot 138. The slider chamber 160 receives the slider 140 and includes an upper contact surface 162 and a friction surface 163. As the slider 140 moves between its stop positions within the slider chamber 160, the upper edge 144 contacts the upper contact surface 162. A center pin 164 is affixed along the upper contact surface 162. The center pin 164 is parallel to the central shaft 87 and is adapted to engaged a detent 166 (FIG. 14) in the upper edge 144 of the slider 140. At a prescribed point between the stop positions, the detent will engage the center pin 164 and thus indicate a neutral sliding position for the vertical pull cable pair. Also, as the slider 140 moves within the slider chamber 160, the friction pad 150 of the slider 140 contacts the friction surface 163 of the slider chamber 160 and generates resistance to the movement of the slider 140. This resistance further helps maintain a desired position of the slider 140 against the tension force of a taut pull cable 32b or 32d.

The two pull cables 32b and 32d of the vertical pull cable pair are attached to the two cable anchors 146, 148 of the slider 140. Pull cable 32b is directly attached to the forward cable anchor 146 and becomes taut when the slider grip 152 (and the slider 140) is moved along the longitudinal axis 81 towards the proximal end of the handle/actuator 12. The other pull cable 32d is guided by a return pulley 168 prior to being attached to the rear cable anchor 148. The return pulley 168 is attached to a pulley axle 170 which is supported in a bore (not shown) in the flat surface 82R of the right handle section 80R and a bore in a pulley cover 174, as shown in FIG. 14. The pulley cover 174 is either formed integrally with the right handle section 80R or otherwise attached to the flat surface 82R at a position which is behind the slider 140 and along the longitudinal axis 81R.

The groove (not shown) of the return pulley 168 lies in a return pulley plane which is parallel to the previously described pulley plane of pulley 96 but lies further from the flat surface 82R than does the pulley plane of pulley 96. The return pulley plane is in alignment with the rear cable anchor 148 of the slider 140.

In the preferred embodiment, the left and right handle sections 80R and 80L, the thumbwheel 92 and the slide grip 152 are made of polyurethane plastic. The return pulley 168, the slider 140, and the cable guide 124 are made from natural derlin plastic. The pulley cover 174 is made from ABS plastic. The detent spring 102, the cable anchors 98, 146 and 148 are made from stainless steel. The lip seal 156 is made from latex plastic. The preload pad 154 is made from a medium silicone sponge of the type manufactured by CHR Industries of New Haven, Conn. (Part No. 200A), laminated to a contact surface made from UHMW polyethylene tape available from McMaster-Carr. (Part No. 76445A14). The friction pad 150 is made from silicone cord stock having a durometer value of 60 and available from Greene Rubber Co.

What is claimed is:

1. A steerable catheter, comprising:
   an elongated flexible shaft having a distal end and a central lumen running the length of the shaft;
   a continuously flexible tip assembly connected to the distal end of said shaft, said tip assembly comprising a proximal section and a distal section, each of said proximal and distal sections having a periphery and a distal end, at least said proximal section including a central lumen, each of said shaft and said proximal and distal sections having a stiffness which is selected to permit said sections to bend substantially independently of each other;
   at least one proximal pull cable and one distal pull cable passing through said central lumen of said shaft to said tip assembly, said proximal pull cable being directed radially from the center lumen of the shaft to the periphery of the proximal section, said distal pull cable passing through the central lumen of said proximal section and being directed radially to the periphery of the distal section;
   means for anchoring said proximal pull cable near the distal end of said proximal section so that tension applied to said proximal pull cable will cause said proximal section of said flexible tip assembly to bend within a first plane; and
   means for anchoring said distal pull cable near the distal end of said distal section so that tension applied to said distal pull cable will cause said distal section of said tip assembly to bend within a second plane.

2. A steerable catheter according to claim 1, wherein said first plane and said second plane are coplanar.

3. A steerable catheter according to claim 1, wherein said first plane and said second plane are perpendicular to each other.

4. A steerable catheter according to claim 1, wherein said first plane and said second plane are not coplanar.

5. A steerable catheter according to claim 1, wherein two proximal pull cables extend through the central lumen of said shaft and are directed radially to the periphery of said proximal section, and wherein both proximal pull cables are anchored near the distal end of said proximal section so that tension applied to one of said proximal pull cables bends said proximal section in a first direction and tension applied to the other of said proximal pull cables bends said proximal section in a direction opposite said first direction.

6. A steerable catheter according to claim 5, wherein two distal pull cables extend through the central lumens of said shaft and proximal section and are directed radially to the periphery of said distal section, and wherein both of said distal pull cables are anchored near the distal end of said distal section so that tension applied to one of said distal pull cables bends said distal section in a first direction and tension applied to the other of said distal pull cables bends said distal section in a direction opposite said first direction.

7. A steerable catheter according to claim 6, wherein said proximal and distal sections each includes a central lumen and at least two outer lumens, and wherein said proximal pull cables are positioned in respective outer lumens of said proximal section and the distal pull cables are positioned in respective outer lumens of said distal section.

8. A steerable catheter according to claim 1, wherein two distal pull cables extend through the central lumens of said shaft and proximal section and are directed radially to the periphery of said distal section, and wherein both of said distal pull cables are anchored near the distal end of said distal section so that tension applied to one of said distal pull cables bends said distal section in a first direction and tension applied to the other of said distal pull cables bends said distal section in a direction opposite said first direction.

9. A steerable electrocardial catheter, comprising:
   an elongated flexible shaft having a central lumen and a distal end;
   a continuously flexible tip assembly connected to the distal end of said shaft, said tip assembly comprising at least a tubular distal section and a tubular proximal section, each having proximal and distal ends and being colinear with said shaft, at least the proximal section having a central lumen, the stiffness of each of said shaft and said distal and proximal sections being selected to provide substantially independent bending of said distal section and/or proximal section;

at least one electrode mounted on said tip assembly;

at least one proximal pull cable extending through the central lumen of said shaft, said proximal pull cable being directed radially to the periphery of the proximal section and being anchored in said tip assembly for bending said proximal section in a predetermined plane without substantially bending said distal section; and at least one distal pull cable extending through the central lumen of said shaft and the central lumen of said proximal section, said distal pull cable being directed radially to the periphery of the distal section, and being anchored in said tip assembly for bending said distal section in a predetermined plane without substantially bending said proximal section.

10. A steerable electrocardial catheter according to claim 9, wherein said predetermined planes are different.

11. A steerable electrocardial catheter according to claim 9, wherein said distal and proximal sections each includes a central lumen and at least one outer lumen wherein at least one electric wire is positioned within said central lumens, said wire being electrically connected to said electrode, and wherein said proximal cable is positioned in an outer lumen of said proximal section and said distal cable is positioned in an outer lumen of said distal section.

12. A steerable electrocardial catheter according to claim 11, wherein said proximal cable is anchored near said distal end of said proximal section and said at least one distal cable is anchored near said distal end of the distal section.

13. A steerable electrocardial catheter according to claim 11, wherein said distal cable passes through the central lumen of said proximal section.

14. A steerable electrocardial catheter according to claim 13, wherein the proximal end of the outer lumen of said proximal section is spaced axially from the distal end of the central lumen of said shaft, and the proximal end of the outer lumen of said distal section is spaced axially from the distal end of the central lumen of said proximal section to facilitate positioning of the cables in their respective lumens.

15. A steerable electrocardial catheter according to claim 14, wherein said cables comprise ultra-high molecular weight polyethylene enveloped by a polyfluoroethylene sheath.

16. A steerable electrocardial catheter according to claim 9, wherein at least two electrodes are mounted on said tip assembly, one of said electrodes being a ring electrode supported on said distal section and the other of said electrodes comprising an electrode cap attached to the distal end of said distal section, and wherein electrical leads connected to said electrodes extend through said tip assembly and shaft.

17. A steerable electrocardial catheter according to claim 9, wherein two proximal pull cables and two distal pull cables are provided, and wherein said distal and proximal sections each includes a central lumen and at least two outer lumens, wherein at least one electric wire is positioned within said central lumens, said wire being electrically connected to said electrode, and wherein said proximal cables are positioned in respective outer lumens of said proximal section and said distal cables are positioned in respective outer lumens of said distal section.

18. A steerable electrocardial catheter according to claim 17, wherein said proximal cables are anchored near said distal end of said proximal section and said distal cables are anchored near said distal end of said distal section.

19. A steerable electrocardial catheter according to claim 17, wherein said distal cables pass through the central lumen of said proximal section.

20. A steerable electrocardial catheter according to claim 19, wherein the proximal ends of the outer lumens of said proximal section are spaced axially from the distal end of the central lumen of said shaft, and the proximal ends of the outer lumens of said distal section are spaced axially from the distal end of the central lumen of the proximal section to facilitate positioning of the pull cables in their respective lumens.

* * * * *

UNITED STATES PATENT AND TRADEMARK OFFICE
CERTIFICATE OF CORRECTION

PATENT NO. : 5,383,852
DATED     : January 24, 1995
INVENTOR(S) : Debbie Stevens-Wright It is certified that error appears in the above-indentified patent and that said Letters Patent is hereby corrected as shown below:

On the title page item [75], after "Fitchburg, Mass.", please add

-- ; Dino F. Cuscuna, Reading, Mass. --

Signed and Sealed this

Twenty-fifth Day of April, 1995

Attest:

BRUCE LEHMAN

*Attesting Officer*         *Commissioner of Patents and Trademarks*